US006747218B2

(12) United States Patent
Huseman et al.

(10) Patent No.: US 6,747,218 B2
(45) Date of Patent: Jun. 8, 2004

(54) ELECTROSURGICAL HAPTIC SWITCH INCLUDING SNAP DOME AND PRINTED CIRCUIT STEPPED CONTACT ARRAY

(75) Inventors: Mark Joseph Huseman, Broomfield, CO (US); James A. Rademacher, Longmont, CO (US)

(73) Assignee: Sherwood Services AG, Schaffhausen (CH)

(*) Notice: Subject to any disclaimer, the term of this patent is extended or adjusted under 35 U.S.C. 154(b) by 66 days.

(21) Appl. No.: 10/251,606

(22) Filed: Sep. 20, 2002

(65) Prior Publication Data

US 2004/0055860 A1 Mar. 25, 2004

(51) Int. Cl.[7] .......................... A61B 18/00; H01H 9/00; H01H 13/64; H01H 13/715

(52) U.S. Cl. .......................... 200/1 B; 200/4; 200/5 R; 200/5 A; 200/52 R; 200/406; 200/292

(58) Field of Search .......................... 200/5 A, 512.517, 200/406, 407, 302.1–302.3, 275, 292, 1 B, 4, 5 R, 1 R; 606/41–48

(56) References Cited

U.S. PATENT DOCUMENTS 2,262,777 A * 11/1941 Roper ........................ 200/406
3,460,539 A 8/1969 Anhalt, Sr.
3,825,004 A 7/1974 Durden, III.
3,828,780 A 8/1974 Morrison, Jr.
3,902,494 A 9/1975 Haberlen et al.
3,906,955 A 9/1975 Roberts
3,967,084 A 6/1976 Pounds ........................ 200/275
3,974,833 A 8/1976 Durden, III
4,021,630 A * 5/1977 Taylor ........................ 200/512
4,032,738 A 6/1977 Esty et al. .................... 606/42
4,046,981 A * 9/1977 Johnson et al. ............. 200/516
4,074,088 A * 2/1978 Keough et al. ............. 200/5 A
4,195,120 A * 3/1980 Rossler et al. ................ 429/50
4,232,676 A 11/1980 Herczog
4,314,559 A 2/1982 Allen
4,331,851 A * 5/1982 Johnson ...................... 200/517
4,352,963 A * 10/1982 De Filippis et al. ........ 200/5 A
4,427,006 A 1/1984 Nottke ........................ 606/42
4,459,443 A 7/1984 Lewandowski ............. 200/407
4,463,234 A 7/1984 Bennewitz .................. 200/516
4,492,231 A 1/1985 Auth
4,562,838 A 1/1986 Walker
4,625,723 A 12/1986 Altnether et al. ............. 606/42
4,640,279 A 2/1987 Beard
4,642,128 A 2/1987 Solorzano
4,683,884 A 8/1987 Hatfield et al.
4,701,193 A 10/1987 Robertson et al.
4,735,603 A 4/1988 Goodson et al.
4,768,284 A * 9/1988 De Filippis et al. .......... 29/622
4,785,807 A 11/1988 Blanch
4,827,911 A 5/1989 Broadwin et al.
4,846,790 A 7/1989 Hornlein et al.

(List continued on next page.)

FOREIGN PATENT DOCUMENTS

FR 2235669 1/1975
WO WO94/20032 9/1994

*Primary Examiner*—J. R. Scott

(57) ABSTRACT

The present disclosure relates to tactile switch assemblies having stepped printed circuit boards for use with snap-domes in surgical instruments. In accordance with one aspect of the present disclosure a tactile switch assembly for use with a surgical instrument includes a substrate, an inner terminal disposed on an upper surface of the substrate and having a first height, an outer terminal disposed on the upper surface of the substrate and substantially surrounding the inner terminal and having a second height which is greater than the height of the inner terminal and a snap-dome secured to the substrate and having a periphery engaged to and in electrical communication with the outer terminal. The snap-dome is depressible through a range wherein, upon inversion of the snap-dome, an apex of the snap dome electrically connect the inner and outer terminals.

9 Claims, 5 Drawing Sheets

U.S. PATENT DOCUMENTS 4,850,353 A 7/1989 Stasz et al.
4,862,890 A 9/1989 Stasz et al.
4,869,715 A 9/1989 Sherburne
4,886,060 A 12/1989 Wiksell
4,901,719 A 2/1990 Trenconsky et al.
4,909,249 A 3/1990 Akkas et al.
4,911,159 A 3/1990 Johnson et al.
4,916,275 A * 4/1990 Almond ...................... 200/516
4,921,476 A 5/1990 Wuchinich
4,931,047 A 6/1990 Broadwin et al.
4,986,839 A 1/1991 Wertz et al.
4,988,334 A 1/1991 Hornlein et al.
5,015,227 A 5/1991 Broadwin et al.
5,026,368 A 6/1991 Adair
5,055,100 A 10/1991 Olsen
5,071,418 A 12/1991 Rosenbaum
5,076,276 A 12/1991 Sakurai et al.
5,088,997 A 2/1992 Delahuerga et al.
5,098,430 A 3/1992 Fleenor ....................... 606/42
5,100,402 A 3/1992 Fan
5,133,714 A 7/1992 Beane
5,147,292 A 9/1992 Kullas et al.
5,160,334 A 11/1992 Billings et al.
5,162,044 A 11/1992 Gahn et al.
5,178,605 A 1/1993 Imonti
5,190,517 A 3/1993 Zieve et al.
5,192,267 A 3/1993 Shapira et al.
5,195,959 A 3/1993 Smith
5,197,962 A 3/1993 Sansom et al.
5,199,944 A 4/1993 Cosmescu
5,217,457 A 6/1993 Delahuerga et al.
5,224,944 A 7/1993 Elliott
5,226,904 A 7/1993 Gentelia et al.
5,233,515 A 8/1993 Cosman
5,234,428 A 8/1993 Kaufman
5,242,442 A 9/1993 Hirschfeld
5,244,462 A 9/1993 Delahuerga et al.
5,254,082 A 10/1993 Takase
5,256,138 A 10/1993 Burek et al.
5,269,781 A 12/1993 Hewell, III
5,306,238 A 4/1994 Fleenor ....................... 606/42
5,312,329 A 5/1994 Beaty et al.
5,318,516 A 6/1994 Cosmescu
5,318,565 A 6/1994 Kuriloff et al.
5,334,183 A 8/1994 Wuchinich
5,376,089 A 12/1994 Smith ..................... 200/505 X
5,380,320 A 1/1995 Morris
5,382,247 A 1/1995 Cimino et al.
5,395,363 A 3/1995 Billings et al.
5,399,823 A 3/1995 McCusker .............. 200/512 X
5,401,273 A 3/1995 Shippert ...................... 606/30
5,403,882 A 4/1995 Huggins
5,406,945 A 4/1995 Riazzi et al.
5,409,484 A 4/1995 Erlich et al.
5,413,575 A 5/1995 Haenggi
5,421,829 A 6/1995 Olichney et al.
5,431,650 A 7/1995 Cosmescu
5,451,222 A 9/1995 De Maagd, deceased et al.
5,460,602 A 10/1995 Shapira
5,462,522 A 10/1995 Sakurai et al.
5,484,398 A 1/1996 Stoddard
5,486,162 A 1/1996 Brumbach
5,498,654 A 3/1996 Shimasaki et al.
5,531,722 A 7/1996 Van Hale
5,549,604 A 8/1996 Sutcu et al.
5,601,224 A 2/1997 Bishop et al.
5,634,912 A 6/1997 Injev
5,643,256 A 7/1997 Urueta
5,669,907 A 9/1997 Platt, Jr. et al.
5,693,050 A 12/1997 Speiser
5,693,052 A 12/1997 Weaver
5,697,926 A 12/1997 Weaver
5,702,360 A 12/1997 Dieras et al.
5,702,387 A 12/1997 Arts et al.
5,713,895 A 2/1998 Lontine et al.
5,720,745 A 2/1998 Farin et al.
5,765,418 A 6/1998 Rosenberg
5,776,092 A 7/1998 Farin et al.
5,797,907 A 8/1998 Clement
5,836,897 A 11/1998 Sakurai et al.
5,843,109 A 12/1998 Mehta et al.
5,868,768 A 2/1999 Wicherski et al.
5,893,862 A 4/1999 Pratt et al.
5,941,887 A 8/1999 Steen et al.
5,944,737 A 8/1999 Tsonton et al.
5,951,581 A 9/1999 Saadat et al.
5,972,007 A 10/1999 Sheffield et al.
6,004,318 A 12/1999 Garito et al.
6,004,333 A 12/1999 Sheffield et al.
6,063,050 A 5/2000 Manna et al.
6,070,444 A 6/2000 Lontine et al.
6,099,525 A 8/2000 Cosmescu
6,117,134 A 9/2000 Cunningham et al.
6,139,547 A 10/2000 Lontine et al.
6,142,995 A 11/2000 Cosmescu
6,146,353 A 11/2000 Platt, Jr.
6,213,999 B1 4/2001 Platt, Jr. et al.
6,251,110 B1 6/2001 Wampler
6,257,241 B1 7/2001 Wampler
6,258,088 B1 7/2001 Tzonev et al.
6,287,344 B1 9/2001 Wampler et al.
6,312,441 B1 11/2001 Deng
6,358,281 B1 3/2002 Berrang et al. ............... 623/10
6,361,532 B1 3/2002 Burek ......................... 606/45
6,402,748 B1 6/2002 Schoenman et al.
6,423,918 B1 * 7/2002 King et al. ................. 200/406
6,489,580 B2 * 12/2002 Yanai et al. ................ 200/406

* cited by examiner

ELECTROSURGICAL HAPTIC SWITCH INCLUDING SNAP DOME AND PRINTED CIRCUIT STEPPED CONTACT ARRAY

BACKGROUND

1. Technical Field

The present disclosure relates generally to printed circuit boards and, more particularly, to a stepped printed circuit board for use with snap-domes in medical devices.

2. Background of Related Art

A wide variety of electrosurgical devices have been developed in the past for use by surgeons during various operations. For example, pulse-like electrosurgical devices have been used for a variety of operations for cauterizing and coagulating tissue during surgery. In addition, apparatii using high frequency or RF pulses (i.e., radio frequency pulses) have been employed for cutting tissue utilizing exposed electrodes having various geometries, e.g., loop wires, needle electrodes, ball-like electrodes, blade-like electrodes and the like. Early electrosurgical devices generally required actuation via foot switches or manual switches which were remotely located relative to the surgical site often requiring the surgeon to seek assistance during the operation.

In order to provide the surgeon with more direct control of the instrument, devices have been developed enabling electrosurgical mode selection and electrosurgical activation of the signals supplied to the electrode (for example, a continuous A.C. signal for cutting or a pulse A.C. signal for coagulating), switches are mounted on the instrument body which allow the surgeon to selectively activate and control the energy emission from the electrosurgical generator. In this manner, the switches permit the surgeon to select varying modes of operation of the same instrument during surgery. The switches are typically sealed to prevent fluids or tissue from contaminating or affecting the interior electronics of the instrument to assure proper operation of concomitant precision and safety during use.

A typical switch for electrosurgical pencil includes a tactile or audible feedback membrane switch, wherein one or both of the switch contacts is/are incorporated into an insulative substrate having a film base on a circuit board panel. The under side of a flexible upper membrane, which overlies the substrate and is spaced apart from the contacts thereon includes a conductive member which may be the other of the switch contacts or a conductive bridge, either of which is adapted to close the contacts upon depression of the flexible membrane.

The problem with tactile or audible feedback membrane switches is that their operation requires a very light force, and a very small deflection in order to complete and close the contact. Thus, without any feedback (i.e., visual, tactile or audible) many operators have difficulty sensing switch closure.

One solution to the problem of tactile feedback or feel has been the introduction of a resilient metal dome which is flexible and which has a certain "snap" when depressed. In use, the marginal edge of the dome is in electrical contact with a first terminal carried by an insulating substrate, while the center of the dome overlies another terminal also carried by the substrate. Upon depression, the central region of the dome contacts the central terminal completing the electrical connection between the two terminals and activating the switch. Upon connection, a simultaneous "snap" is either felt in the surgeon's finger or heard.

Other prior art designs have used an embossed plastic bubble rather than a metal dome which is overlaid on the membrane switch or on a separate layer between the membrane and the overlay. One drawback to the plastic bubble concept is that the plastic bubble often produces undesirable tactile characteristics because it does not uniformly deflect over its entire area. Since the bubble does not deform consistently toward the center, an undesirable "teasing" effect may occur. Switch teasing is undesirable because the operator may receive an acceptable tactile feel response, yet the switch may not close properly or consistently.

Another drawback in the use of the plastic bubble concept is the lack of effective tactile feedback. In other words, it may be difficult to sense (tactically) actual electrical contact with the underlying printed circuit board upon depression of the plastic dome. Moreover, current printed circuit board designs utilize domes having a single plane deposition thickness on the board which further limits overall tactile feedback.

While there have been many attempts to produce suitable and effective electrosurgical devices with finger-operated tactile feedback switches, there exists a need to develop a feedback switch and circuit board arrangement which, when depressed, effectively completes the electrical circuit and provides reliable sensory feedback to the surgeon during use.

SUMMARY

The present disclosure is directed to stepped printed circuit board snap-domes for use in medical devices in order to improve the tactile feedback to a surgeon operating a surgical instrument on which the snap-dome is mounted.

In accordance with one aspect of the present disclosure a tactile switch assembly for use with a surgical instrument includes a substrate, an inner terminal disposed on an upper surface of the substrate and having a first height, an outer terminal disposed on the upper surface of the substrate and substantially surrounding the inner terminal and having a second height which is greater than the height of the inner terminal and a snap-dome secured to the substrate and having a periphery engaged to and in electrical communication with the outer terminal. The snap-dome is depressible through a range wherein, upon inversion of the snap-dome, an apex of the snap dome electrically connect the inner and outer terminals.

Preferably, the snap-dome is connected to the outer terminal at a plurality of contact points. It is envisioned that the outer terminal is substantially ring-like and the outer peripheral edge of the snap-dome is contiguous therewith.

Preferably, the tactile switch assembly further includes an electrosurgical regulator which regulates the amount of electrosurgical energy transmitted upon activation of the tactile switch.

In another aspect of the present disclosure, the tactile switch assembly includes a substrate made of a non-conductive material, a first inner terminal, a second inner terminal and an outer terminal. The first inner terminal is disposed on an upper surface of the substrate and is made from a conductive material defining a first height. The second inner terminal is disposed on the upper surface of the substrate and is internal of the first inner terminal. The second inner terminal is made from a conductive material and defines a second height which is less than the height of the first inner terminal. The outer terminal is disposed on the upper surface of the substrate and substantially surrounds the first inner terminal. The outer terminal is made from a conductive material and defines a third height which is greater than the first height of the first inner terminal.

The tactile switch assembly according to the present aspect of the disclosure further includes a snap-dome secured to the substrate and having a periphery engaged to and in electrical communication with the outer terminal. The snap-dome is depressible through a range wherein, upon depression of the snap-dome, an apex of the snap-dome electrically interconnects the first inner terminal and the outer terminal. Moreover, upon continued depression the apex of the snap-dome electrically interconnects the second inner terminal and the outer terminal.

In yet another aspect there is disclosed a printed circuit board for use with a snap-dome switch of a medical instrument. The printed circuit includes a non-conductive substrate defining an upper surface, a first conductive terminal disposed on the upper surface of the substrate, wherein the first conductive terminal defines a first height, and a second conductive terminal disposed on the upper surface of the substrate, wherein the second conductive terminal defines a second height which is greater than the height of the first conductive terminal. Preferably, the second conductive terminal is generally concentrically spaced from the first conductive terminal.

It is envisioned that the snap-dome is contiguous with the second conductive terminal. Preferably, the snap-dome is depressible through a range wherein upon inversion of the snap-dome an apex of the snap-dome electrically connects the first and second terminals.

In an alternative embodiment, the tactile switch assembly includes a substrate, a plurality of contact pads disposed on an upper surface of the substrate, a turntable rotatably mounted on the upper surface of the substrate, an inner terminal disposed on an upper surface of the turntable, an outer terminal disposed on the upper surface of the substrate and substantially surrounding the inner terminal, the outer terminal having an electrical lead extending therefrom and being electrically contactable with a selected one of the plurality of contact pads and a snap-dome secured to the turntable and having a periphery engaged to and in electrical communication with the outer terminal.

Preferably, the substrate and the turntable are made from non-conductive materials while each contact pad, the inner terminal and the outer terminal are made from conductive materials. Preferably, each contact pad is electrically connected to an electrosurgical energy source.

These and other objects will be more clearly illustrated :below by the description of the drawings and the detailed description of the preferred embodiments.

BRIEF DESCRIPTION OF THE DRAWINGS

Other objects and features of the present invention will become apparent from the following detailed description considered in connection with the accompanied drawings. It should be understood, however, that the drawings are designed for the purpose of illustration only and not as a definition of the limits of the invention.

DETAILED DESCRIPTION OF PREFERRED EMBODIMENTS

Figure 1A:
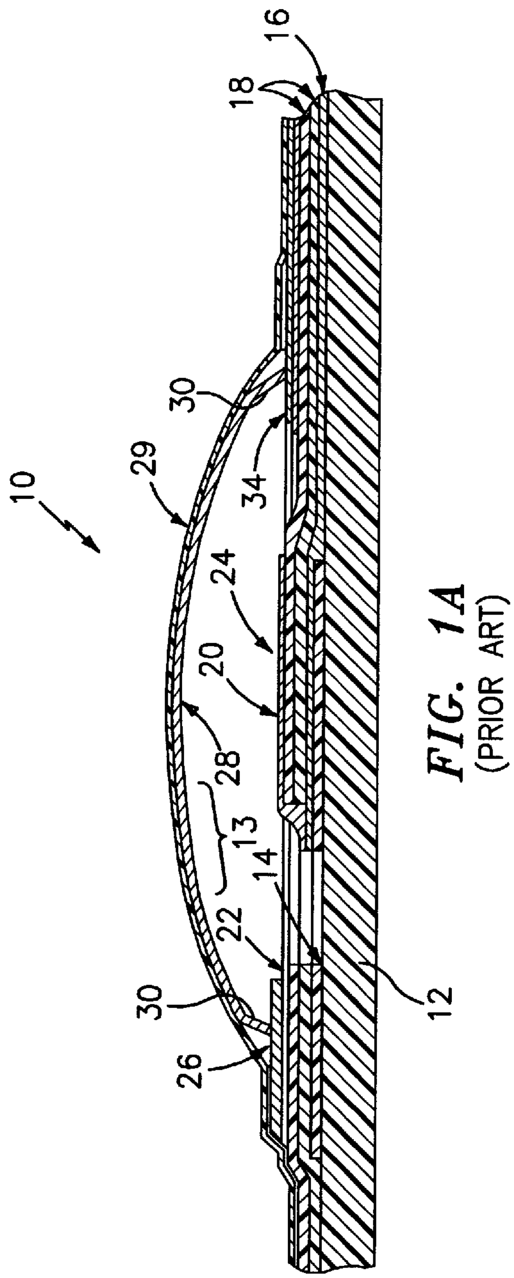
FIG. 1A (PRIOR ART)
FIG. 1A is a side, cross-sectional view of a prior art tactile membrane switch assembly.

Preferred embodiments of the presently disclosed stepped printed circuit board for use in connection with snap domes is described in detail herein with reference to the figures wherein like reference numerals identify similar or identical elements.

Referring initially to FIG. 1A, a tactile membrane switch according to a prior art device assembly is generally identified as switch assembly 10. Switch assembly 10 includes a substrate of electrically insulating material 12 having layers of non-conductive (dielectric) ink and conductive ink defined thereon which form an electrical circuit 13. Circuit 13 includes at least one inner contact 24 and at least one outer contact 26. Preferably, electrical circuit 13 is formed by initially applying a first dielectric layer 14 and subsequently forming additional conductive and dielectric layers in a pattern thereon, e.g., first conductive layer 16, second dielectric layer 18, second conductive layer 20 and carbon conductive layer 22.

A snap dome switch 28 having a predetermined outer perimeter edge 30 is mounted atop switch assembly 10 such that edge 30 connects to outer contact 26. When the snap dome is depressed, the snap dome completes the electrical circuit between inner contact 24 and outer contact 26. Preferably, snap dome switch 28 is made of a suitable metal or conductive material and configured so that when depressed, a predetermined range of motion is evident to the surgeon (tactile feedback) through a snap phase of closing the electrical circuit. The surgeon develops a tactile "feel" through the range of motion -and during activation of the switch when depressed and deflected over the center position. Preferably, snap dome switch 28 includes a dielectric outer layer 29 which protects the surgeon from electrical shock during use and reduces the chances of contaminating the switch with surgical fluids.

Figure 1B:
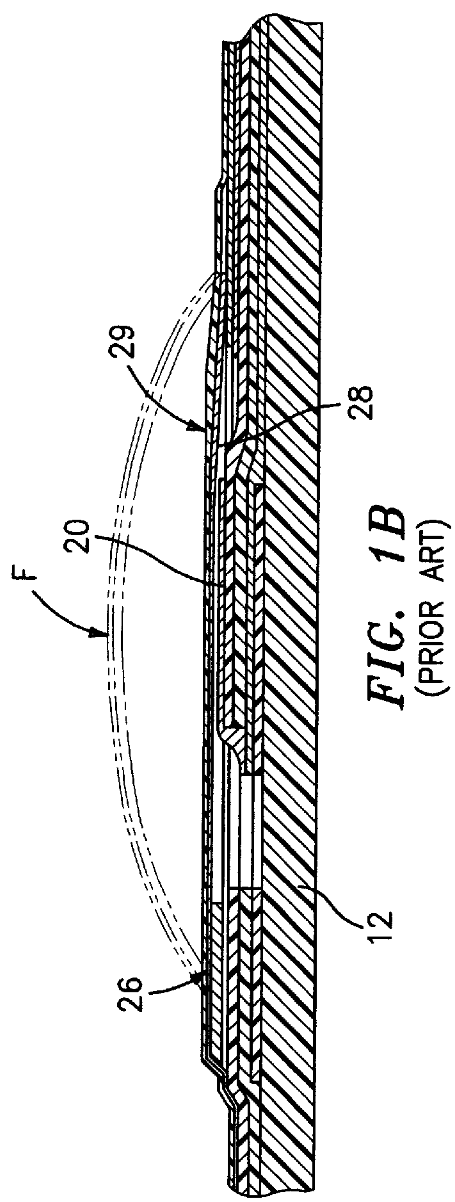
FIG. 1B (PRIOR ART)
FIG. 1B is a side, cross-sectional view of the tactile membrane switch assembly of FIG. 1A, shown in the depressed or contact position.

As shown best in FIGS. 1A and 1B, the center area in dielectric layer 18 is typically smaller than the center area of layer 16, thus allowing the center area of layer 20 to electrically connect to the center layer 16. Inner and the outer contacts 24 and 26 are disposed atop layer 18 at about the same height to assure consistent electrical contact when the snap dome is depressed to a substantially flat orientation (FIG. 1B). More particularly, depressing snap dome 28 causes the center of snap dome 28 to snap and engagably contact inner contact 24 which electrically connects inner and outer contacts 24, 26, respectively.

Figure 2:
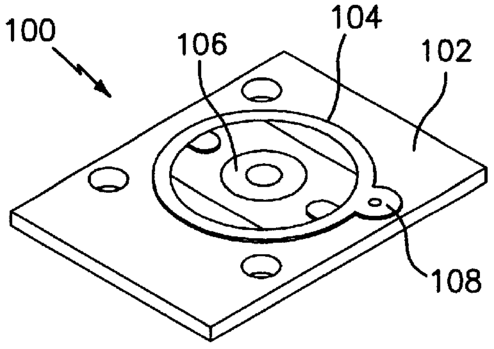
FIG. 2 is a top, perspective view of a printed circuit board in accordance with the present disclosure.
Figure 3:
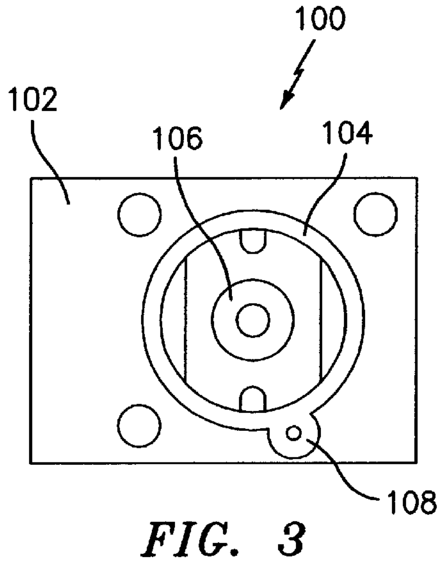
FIG. 3 is a top, plan view of the printed circuit board shown in FIG. 2.
Figure 4:
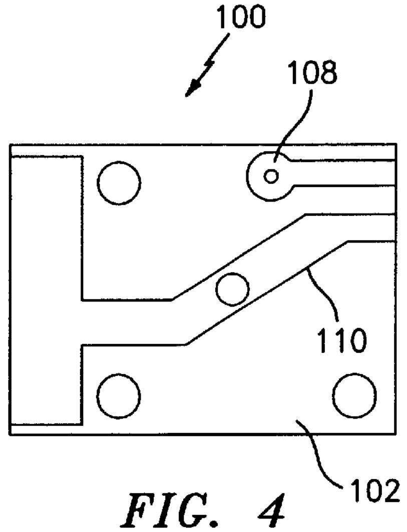
FIG. 4 is a bottom, plan view of the printed circuit board shown in FIG. 2.
Figure 5:
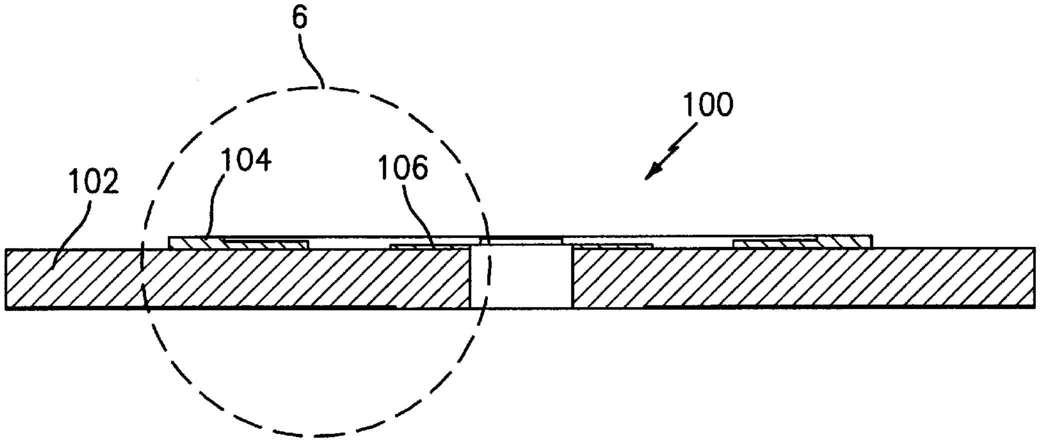
FIG. 5 is a side, cross-sectional view, of the printed circuit board shown in FIG. 3.
Figure 6:
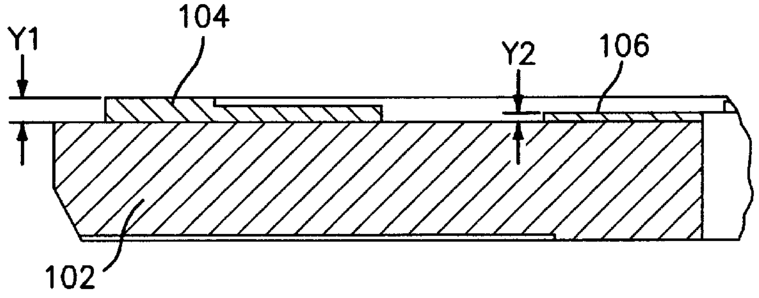
FIG. 6 is an enlarged, side view of the area in detail of FIG. 5.

FIGS. 2–6 show a stepped printed circuit board 100 in accordance with the present disclosure for use in connection with a snap dome switch. Stepped printed circuit board 100 includes a substrate 102 preferably made from electrically insulating material such as polyester on which layers of dielectric and conductive ink are printed thereon (e.g., screen printed) to define a circuit pattern. It is envisioned that substrate 102 can be fabricated from either a rigid or a flexible insulating material. More particularly and as best seen in FIGS. 2–4, the layering process preferably forms an outer substantially circular contact terminal 104 and an inner substantially circular contact terminal 106. Outer terminal 104.includes an electrical lead 108 which extends through substrate 102 for connection to an electrosurgical energy source and inner terminal 106 includes an electrical lead 110 (see FIG. 4) which extends through substrate 102 for connection to the same or alternate electrosurgical energy source. While a continuous outer circular terminal and an inner circular terminal has been disclosed herein, other geometric configurations for one or both the inner and outer terminals is envisioned, e.g., arcuate, semicircular, and the like.

Preferably, outer terminal 104 and inner terminal 106 are patterned on substrate 102 by conventional screen printing techniques. Preferably, printed circuit board 100 is constructed using known photo-masking techniques, wherein a photo-mask is applied to the desired dielectric surfaces of substrate 102 and no photo-mask is applied to the desired conductive surfaces of substrate 102. Accordingly, printed circuit board 100 is constructed by first applying at least one photo-mask to the surface of substrate 102 and covering the areas between outer terminal 104 and inner terminal 106. After a first layer of conductive material is applied to substrate 102 to form inner terminal 106 and partially form outer terminal 104, at least one additional photo-mask is applied over substrate 102 to cover inner terminal 106 and the space between outer terminal 104 and inner terminal 106. Thereafter, at least one additional layer of conductive material is applied to substrate 102, thereby forming the remainder of the printed circuit board 100. Other masking techniques are also envisioned for forming the printed circuit board 100.

As shown, outer terminal 104 is formed by layering a plurality of successive layers of one or more conductive and/or dielectric materials atop one another to define a height "Y1". Inner terminal 106 is also formed by layering a plurality of successive layers of conductive and/or dielectric materials atop one another to define a height "Y2" which is less than height "Y1" (see FIG. 6). Each layer is applied in registration with the previous layer so as to correctly and accurately define switch sites and conductive runs and appropriately insulate the contacts of each switch site from one another. It is contemplated that outer terminal 104 be made up of five layers of conductive and/or dielectric materials, while inner terminal 106 is made up of two or three layers of conductive and/or dielectric materials. In this manner, as seen best in FIGS. 5 and 6, the contact surface of inner terminal 106 is recessed relative to the contact surface of outer terminal 104. For example, outer terminal 104 may include a height "Y1" in a range of about 0.0025 inches to about 0.0075 inches and preferably about 0.0038 inches, while inner terminal 106 may include a height "Y2" in a range of about 0.0005 inches to about 0.0025 inches and preferably about 0.0014 inches. As can be appreciated, arranging the inner and outer terminals in this manner creates a step-like circuit pattern between the inner and outer terminals 106, 104.

Figure 7:
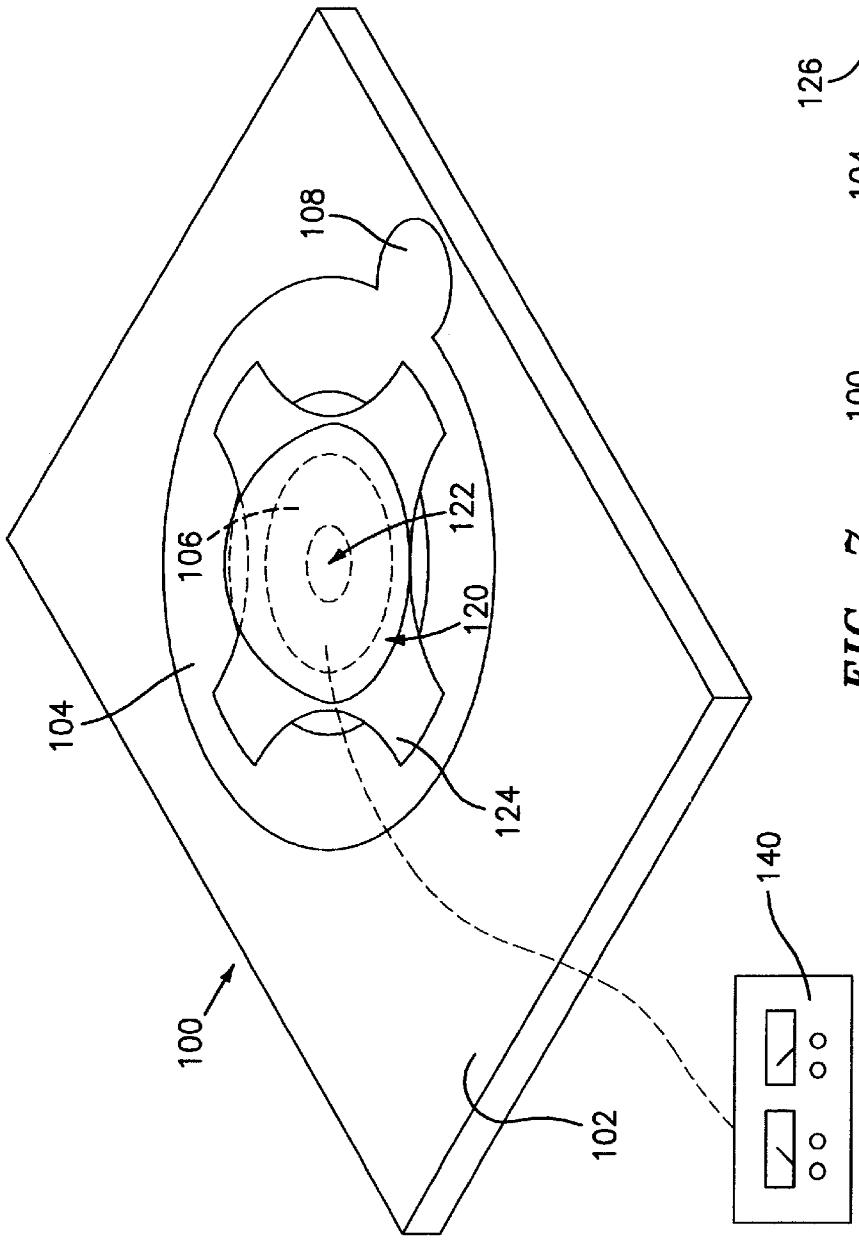
FIG. 7 is a top, perspective view of the printed circuit board of FIG. 2 having a snap-dome mounted to a surface thereof.
Figure 8:
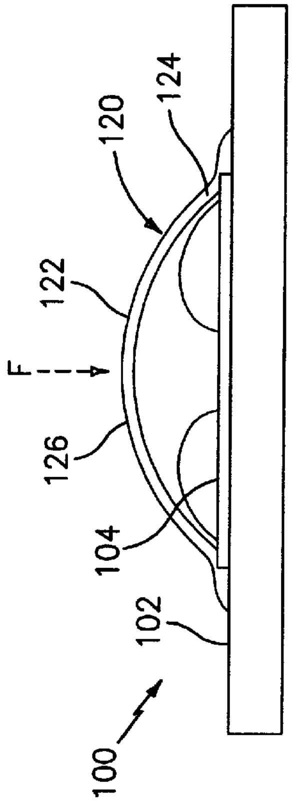
FIG. 8 is a side, cross-sectional view of the printed circuit board and snap-dome of FIG. 7.

As best seen in FIGS. 7 and 8, snap-like tactile feedback member 120, e.g., snap dome, is mounted to stepped printed circuit board 100 in electrical communication with outer terminal 104 and in vertical registration with inner terminal 106. More particularly, snap-dome 120 includes an apex 122 and a plurality of feet-like contacts 124 which attach to outer terminal 104. Preferably, apex 122 and feet 124 are made from electrically conductive material and are in electrical communication with one another. A thin layer of elastomeric/flexible insulating or non-conductive material 126 (see FIG. 8) coats the outer surface of dome 120 and secures dome 120 to substrate 102. Feet 124 are located in corresponding space-opposed regions of snap dome 120 and deform downwardly when snap dome 120 is depressed. While a dome 120 having four feet 124 is shown and described, it is contemplated that dome 120 can have any number of feet 124 or can terminate in a continuous terminal edge all the way around. It is further envisioned that snap dome 120 can be any geometric shape other than hemi-spherical as shown in the figures, such as, for example, hemi-cylindrical.

When mounted atop printed circuit board 100, feet 124 of snap dome 120 are physically and electrically in contact with outer terminal 104 and apex 122 (i.e., the central region of the dome) resides in vertical registration over inner terminal 106. Upon depression, snap dome 120 deflects downwardly to a point where apex 122 passes the plane of outer terminal 104 and inverts into contact with inner terminal 106. As can be appreciated, the point of inversion as well as the additional range of travel of the membrane provides an enhanced level of tactile feedback to the user thus enabling the user to more readily ascertain the "active" position of the switch. Moreover, it is envisioned that the snap dome may be dimensioned such that the point of inversion of the snap dome can be coupled with a physical and audible "snap" which can be readily felt or heard by the surgeon thus enhancing the surgeon's control over the activation of the instrument.

More particularly, snap dome 120 is made from a suitable metal or conductive material and configured so that when depressed, true tactile feedback will be sensed by the user when the dome goes through the "snap phase" to close the circuit. As discussed above, the initial tactile "feel" comes from a sudden decrease in force during actuation of apex 122 of snap dome 120 when depressed in the direction "F" over inner terminal 106. However, in accordance with the stepped printed circuit board 100 design disclosed herein, a second tactile "feel" is apparent when apex 122 passes the horizontal plane defined by outer terminal 104, i.e., point of inversion. Upon removal of the force "F", the snap dome and membrane 120 return to the original configuration. Thus, according to the present disclosure, an invertable snap-dome, in combination with the novel stepped printed circuit board disclosed herein, greatly enhances the overall tactile feedback to the surgeon. Moreover, the surgeon can more readily "feel" the "on" and "off" positions of the instrument due to the greater range of travel of apex 122 over conventional snap domes wherein the outer and inner terminals reside in approximately the same plane.

The dimensions and configuration of snap dome 120 is crucial in order to ensure consistent repetitive operation thereof. Many factors contribute to the consistent repetitive operation of snap dome 120, including for example, the material selected, the thickness of the snap dome, the topographical profile of the snap dome, the shape of the dome, the number of feet, the particular arrangement of the feet relative to one another and the overall dimensions (i.e., height of the apex above the printed circuit board, diameter, length, width, etc.).

Figure 9:
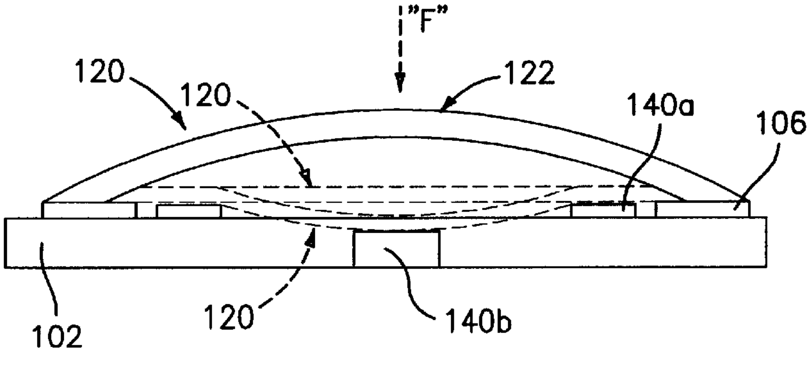
FIG. 9 is side, cross-sectional view of the printed circuit board of FIG.7, shown with the snap-dome in the depressed or contact position.

It is envisioned that snap-dome 120 can be configured and adapted to have more than two-stages as described above. In this manner, the amount of energy being transmitted or the specific operation being performed (i.e., coagulation or cutting) can be selected depending on the position of the apex of the snap-dome. For example, FIG. 9 shows one embodiment wherein the printed circuit board includes two inner terminals 106*a*, 106*b* and which are application specific. More particularly, as apex 122 moves through the range of travel, the outer periphery of apex 122 initially contacts inner terminal 140*a* which transmits a first level of electrosurgical energy to the instrument to coagulate tissue. Further movement of apex 122, through the range of travel, causes apex 122 to invert and contact a second inner terminal 140*b* which transmits additional electrosurgical energy to the instrument to cut tissue.

It is envisioned that the stepped printed circuit board, in accordance with the present disclosure will be used in connection with surgical equipment and, in particular with electrosurgical equipment. Preferably, the stepped printed circuit boards disclosed herein are sealed within the electrosurgical instrument housing. Moreover, it is envisioned that the one of the terminals, e.g., inner terminal 106, may be coupled to a switch regulator 140 (FIG. 7) which allows the surgeon to regulate the amount of electrosurgical energy delivered through the surgical instrument upon activation of the snap dome switch 120. For example, regulator 140 may include a dial which has predetermined positions which relate to predetermined electrosurgical energy levels for "cutting" or "coagulating" tissue.

Figure 10:
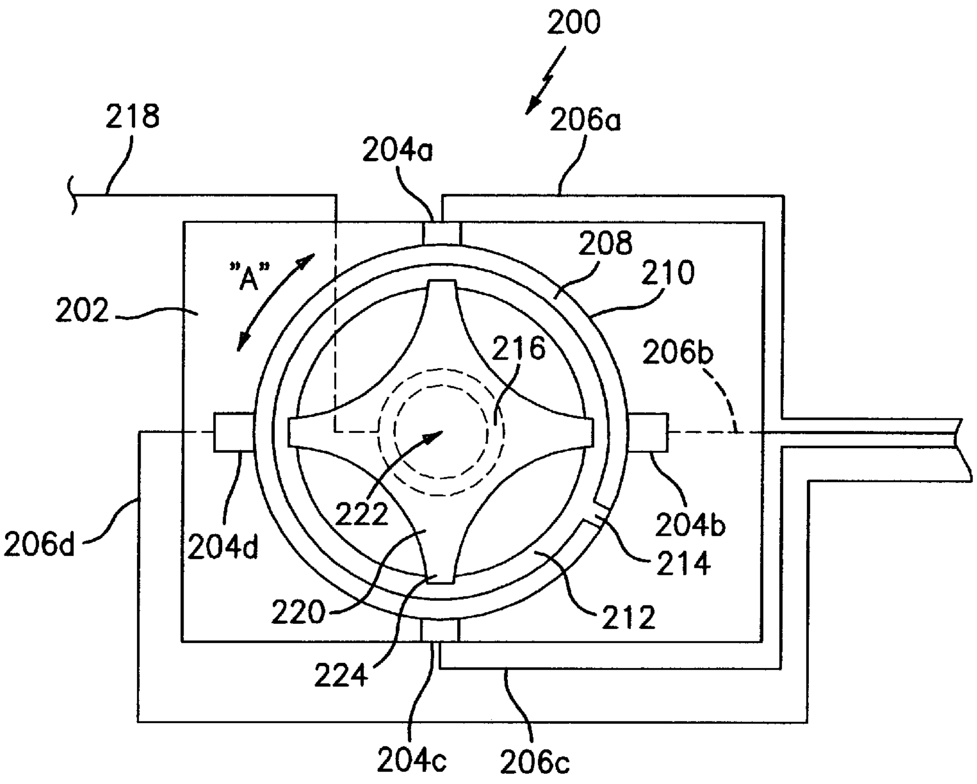
FIG. 10 is a top, plan view of a printed circuit board and snap-dome in accordance with an alternate embodiment of the present disclosure.

Turning now to FIG. 10, a stepped printed circuit board 200 in accordance with an alternate embodiment of the present disclosure for use in connection with a snap dome switch is shown. Stepped printed circuit board 200 includes a substrate 202, preferably made from electrically insulating material having a plurality of electrically conductive contact pads 204*a*–204*d* provided thereon. While four contact pads are shown disposed on substrate 202, it is envisioned that any number of contact pads can be provided. Each contact pad 204*a*–204*d* includes a respective electrical lead 206*a*–206*d* which extends through substrate 202 for connection to an electrosurgical energy source. It is envisioned that each contact pad 204*a*–204*d* results in the activation of a different electrosurgical function, such as for example, cutting, coagulating, sealing, etc.

Printed circuit board 200 further includes a turntable 208 rotatably coupled thereto. Turntable 208 is preferably circular and is defined by a terminal edge 210. While a circular turntable 208 is preferred, turntables having other geometric configurations, such as, for example, triangular, square, rectangular, polygonal and the like are envisioned. Turntable 208 is preferably made from an electrically insulating material and includes an electrically conductive outer terminal 212 disposed thereon having an electrical lead 214 extending radially outwardly therefrom. Preferably, electrical lead 214 extends through turntable 208 to electrically contact a respective one of the plurality of contact pads 204*a*–204*d* of substrate 202. Accordingly, as turntable 208 is rotated, electrical lead 214 of turntable 208 is selectively brought into electrical contact with one of the plurality of contact pads 204*a*–204*d* of substrate 202. While a single electrical lead 214 is shown, it is envisioned that any number of electrical leads can be provided. It is further envisioned that turntable 208 is slidably mounted to substrate 202 in order to activate various other contacts and the like.

Printed circuit board 200 further includes an electrically conductive inner terminal 216 disposed thereon. Similar to printed circuit board 100, inner terminal 216 is disposed within outer terminal 212. Preferably, inner terminal 216 has a height which is less than a height of outer terminal 212. Inner terminal 216 includes an electrical lead 218 which extends through substrate 202 for connection to the same or an alternate electrosurgical energy source. Printed circuit board 200 is constructed in such a manner that as turntable 208 rotates atop substrate 202 an electrical connection is maintained between inner terminal 216 and electrical lead 218.

A snap-like tactile feedback member 220 (i.e., snap dome 220), similar to snap dome 120 described above, is mounted atop turntable 208. Snap dome 220 is preferably in electrical communication with outer terminal 212 and in vertical registration with inner terminal 218. Preferably, snap dome 220 includes an apex 222 and a plurality of feet-like contacts 224 which attach to outer terminal 212. When mounted atop turntable 208, feet 224 of snap dome 220 are physically and electrically in contact with outer terminal 212 and apex 222 resides in vertical registration over inner terminal 216.

In use, the surgeon rotates turntable 208 in either a clockwise or a counter clockwise direction, as indicated by double headed arrow "A", in order to select a desired function of an electrosurgical instrument to which printed circuit board 200 is mounted. By rotating turntable 208, the surgeon effectively aligns and established an electrical connection between electrical lead 214 of turntable 208 and a selected one of the plurality of contact pads 204*a*–204*d*. Accordingly, alignment of electrical lead 214 with a selected one of the plurality of contact pads 204*a*–204*d* results in selection of an alternate electrosurgical function (i.e., cutting, coagulating, sealing, etc.). As such, the surgeon can select the function desired directly from the electrosurgical unit.

It is envisioned that indicia (not shown) can be provided on the outer surface of snap dome 220 and radially aligned with electrical lead 214 of turntable 208 in order to provide the surgeon with a visual indication as to the position of electrical lead 214. It is further envisioned that separate identifying indicia can be provided in the vicinity of each of the plurality of contact pads 204*a*–204*d* in order to provide the surgeon with an indication as to what function snap dome 220 has been rotated to.

It is contemplated that turntable 208 and substrate 202 are configured and adapted such that turntable 208 "snaps" into a selected position (i.e., a position in which electrical lead 214 is aligned with a selected one of the plurality of contact pads 204*a*–204*b*) as the surgeon rotates turntable 208. For example, substrate 202 can be provided with a plurality of recesses (not shown), corresponding to each of the contact pads 204*a*–204*d*, formed in the surface thereof while turntable 208 includes a projection (not shown), configured and adapted to be received within a selected one of the plurality of recesses, extending from a bottom surface thereof. In use, as turntable 208 is rotated, the projection travels from recess to recess. Moreover, the projection/recess combination provides the surgeon with a tactile feel as to the when turntable 208 is in a selected position.

While embodiments of stepped printed circuit boards according to the present disclosure have been described herein it is not intended that the disclosure be limited thereto and the above description should be construed as merely exemplifications of preferred embodiments. Those skilled in the art will envision other modifications within the scope and spirit of the present disclosure.

What is claimed is:

1. A tactile switch assembly for use with a surgical instrument, comprising:

a substrate made of a non-conductive material;

an inner terminal disposed on the upper surface of the substrate, the inner terminal being made from a conductive material and having a first height from the upper surface;

an outer terminal disposed on the upper surface of the substrate and substantially surrounding the inner terminal, the outer terminal being made from a conductive material and having a second height from the upper surface of the substrate, the second height being greater than the height of the inner terminal; and a snap-dome secured to the substrate and having a periphery engaged to and in electrical communication with the outer terminal, the snap-dome being depressible through a range wherein, upon inversion of the snap-dome, an apex of the snap-dome electrically connects the inner and outer terminals.

2. The tactile switch assembly according to claim 1, wherein the periphery of the snap-dome defines a plurality of discrete contact points extending therefrom, wherein the snap-dome is in electrical communication with the outer terminal via the plurality of discrete contact points.

3. The tactile switch assembly according to claim 2, wherein the outer terminal is substantially ring-like and the outer peripheral edge of the snap-dome is contiguous therewith.

4. The tactile switch assembly according to claim 1, further comprising an electrosurgical regulator electrically connected to the inner terminal, the electrosurgical regulator being configured and adapted to regulate the amount of electrosurgical energy transmitted upon activation of the tactile switch.

5. A tactile switch assembly for use with a surgical instrument, comprising:

a substrate made of a non-conductive material;

a first inner terminal disposed on an upper surface of the substrate, the first inner terminal being made from a conductive material and having a first height;

a second inner terminal disposed on the upper surface of the substrate and internal of the first inner terminal, the second inner terminal being made from a conductive material and having a second height which is less than the height of the first inner terminal;

an outer terminal disposed on the upper surface of the substrate and substantially surrounding the first inner terminal, the outer terminal being made from a conductive material and having a third height which is greater than the first height of the first inner terminal; and a snap-dome secured to the substrate and having a periphery engaged to and in electrical communication with the outer terminal, the snap-dome being depressible through a range wherein, upon depression of the snap-dome, an apex of the snap-dome electrically interconnects the first inner terminal and the outer terminal and upon continued depression the apex of the snap-dome electrically interconnects the second inner terminal and the outer terminal.

6. A printed circuit board for use with a snap-dome switch of a medical instrument, the printed circuit board comprising:

a non-conductive substrate defining an upper surface;

a first conductive terminal disposed on the upper surface of the substrate, the first conductive terminal defining a first height from the upper surface; and a second conductive terminal disposed on the upper surface of the substrate, the second conductive terminal defining a second height from the upper surface, the second height being greater than the height of the first conductive terminal, the second conductive terminal being generally concentrically spaced from the first conductive terminal.

7. The printed circuit board according to claim 6, wherein the snap-dome is contiguous with the second conductive terminal.

8. The printed circuit board according to claim 7, wherein the snap-dome is depressible through a range wherein upon inversion of the snap-dome an apex of the snap-dome electrically connects the first and second terminals.

9. A tactile switch assembly for use with an electrosurgical instrument, comprising:

a substrate made from a non-conductive material;

a plurality of contact pads disposed on an upper surface of the substrate, each contact pad being electrically connected to an electrosurgical energy source;

a turntable made from a non-conductive material, the turntable being rotatably mounted on the upper surface of the substrate;

an inner terminal disposed on an upper surface of the turntable, the inner terminal being made from a conductive material;

an outer terminal disposed on the upper surface of the turntable and substantially surrounding the inner terminal, the outer terminal having an electrical lead extending therefrom and being electrically contactable with a selected one of the plurality of contact pads upon rotation of the turntable; and a snap-dome secured to the turntable and having a periphery engaged with and in electrical communication with the outer terminal.

* * * * *